United States Patent
Kaethner et al.

(10) Patent No.: US 12,193,771 B2
(45) Date of Patent: Jan. 14, 2025

(54) METHOD FOR GENERATING AN ACTUATION SIGNAL FOR A ROBOTIC SYSTEM FOR ROBOT-ASSISTED NAVIGATION OF A MEDICAL OBJECT AND OVERALL SYSTEM

(71) Applicant: Siemens Healthcare GmbH, Erlangen (DE)

(72) Inventors: Christian Kaethner, Forchheim (DE); Michael Wiets, Langensendelbach (DE); Andreas Meyer, Bubenreuth (DE)

(73) Assignee: Siemens Healthineers AG, Forchheim (DE)

( * ) Notice: Subject to any disclaimer, the term of this patent is extended or adjusted under 35 U.S.C. 154(b) by 388 days.

(21) Appl. No.: 17/851,332

(22) Filed: Jun. 28, 2022

(65) Prior Publication Data

US 2022/0409309 A1 Dec. 29, 2022

(30) Foreign Application Priority Data

Jun. 29, 2021 (DE) ...................... 10 2021 206 726.3

(51) Int. Cl.
*A61B 34/30* (2016.01)
*A61B 6/00* (2024.01)
(Continued)

(52) U.S. Cl.
CPC ............... *A61B 34/30* (2016.02); *A61B 6/12* (2013.01); *A61B 6/5229* (2013.01);
(Continued)

(58) Field of Classification Search
None
See application file for complete search history.

(56) References Cited

U.S. PATENT DOCUMENTS 10,779,889 B2 * 9/2020 Kowarschik ........... A61B 6/504
2007/0249911 A1 10/2007 Simon
(Continued)

FOREIGN PATENT DOCUMENTS

| EP | 2015845 B1 | 11/2017 |
| EP | 3406291 B1 | 12/2019 |

OTHER PUBLICATIONS

S. Hasanzadeh, Backlash characterization and position control of a robotic catheter manipulator using experimentally-based kinematic model. (Year: 2017).*

(Continued)

*Primary Examiner* — Jaime Figueroa
*Assistant Examiner* — Arslan Azhar
(74) *Attorney, Agent, or Firm* — Lempia Summerfield Katz LLC

(57) ABSTRACT

A system and method for generating an actuation signal for a robotic system for robot-assisted navigation of a medical object with a curved tip in a hollow organ of a patient. An an X-ray system for image monitoring of the intervention is assigned to the robotic system. The method includes determining a current relative position and relative orientation of the curved tip of the object relative to the hollow organ using the X-ray system, calibrating the robotic system on the basis of the determined current relative position and relative orientation of the tip of the object relative to the hollow organ, retrieving first information on a planned path section in the hollow organ, retrieving second information on at least one relative position and relative orientation or relative position sequence and relative orientation sequence of the curved tip of the same or a similar object relative to the hollow organ used during a navigation movement along at least one previously traversed path section in the hollow organ or another hollow organ from a memory unit, and (Continued)

generating an actuation signal for actuating the robotic system. The actuation takes account of the first and second information and the current relative position and relative orientation of the tip relative to the hollow organ.

19 Claims, 4 Drawing Sheets

(51) Int. Cl.
    *A61B 6/12*           (2006.01)
    *A61B 90/00*         (2016.01)
    *G06T 7/00*           (2017.01)

(52) U.S. Cl.
    CPC ...... *G06T 7/0012* (2013.01); *A61B 2034/301* (2016.02); *A61B 2090/376* (2016.02)

(56) References Cited

U.S. PATENT DOCUMENTS

| | | | |
|---|---|---|---|
| 2010/0069833 A1 | 3/2010 | Wenderow et al. | |
| 2015/0302166 A1* | 10/2015 | Thomson | G16H 50/50 703/2 |
| 2020/0110936 A1* | 4/2020 | Hares | A61B 1/0005 |
| 2020/0315491 A1* | 10/2020 | Mooiweer | A61B 5/7285 |

OTHER PUBLICATIONS

Lucio Pancaldi, Flow driven robotic navigation of microengineered endovascular probes. (Year: 2020).*

* cited by examiner

METHOD FOR GENERATING AN ACTUATION SIGNAL FOR A ROBOTIC SYSTEM FOR ROBOT-ASSISTED NAVIGATION OF A MEDICAL OBJECT AND OVERALL SYSTEM

CROSS REFERENCE TO RELATED APPLICATIONS

This application claims the benefit of DE 102021206726.3 filed on Jun. 29, 2021, which is hereby incorporated by reference in its entirety.

FIELD

Embodiments relate to a method and apparatus for generating an actuation signal for a robotic system for robot-assisted navigation of a medical object.

BACKGROUND

Interventional medical procedures in or via the vascular system of a patient's body require medical objects to be introduced into the vascular system via percutaneous vascular access (for example, guide wires or instruments such as catheters) and guided to the target region to be treated. This may be supported by a medical imaging system, for example an X-ray imaging system, that allows the practitioner to monitor and track the progress of the treatment, such as the position of the object, using real-time image data. As a development of manual navigation of the objects in the vascular system, a robotic system is connected between the hands of the practitioner and the patient, with the advantage that the practitioner no longer has to stand directly at the positioning table for the patient, but may maneuver the objects (rotational movement, forward movement and backward movement) remotely. Such robotic systems by which robotic assisted (semi)automatic movement of an object may be affected in a cavity organ of a patient are known in principle, for example from EP 3406291 B1.

Robotic systems frequently include at least one robot control unit and a robot-assisted drive system with a drive and a drive mechanism. However, after the introduction of the medical object, for example a medical wire with a defined curved tip, the robotic system does not know the alignment of the introduced object, i.e., the relative orientation of the curved tip to the hollow organ. Thus, in the case of a curved wire, it may be the case that this is oriented with respect to its curvature, for example parallel or at a certain angle to the table plane of an imaging system. This is in particular of interest when the robotic system is required to act as autonomously as possible and the trial or error rate is required to be minimized, especially at complicated or possibly even critical points in the vascular system, for example kinks, bends or outlets of the hollow organ, of the patient.

BRIEF SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide a method and a system where a robotic system may navigate a medical object with a curved tip in a hollow organ of a patient in a manner that is as error-free and patient-friendly as possible.

The method includes generating an actuation signal for a robotic system for robot-assisted navigation of a medical object, for example medical wire or catheter, with a curved tip in a hollow organ of a patient. An X-ray system for image monitoring of the intervention is assigned to the robotic system. The method includes determining a current position and orientation of the curved tip of the object using the X-ray system, for example by recording and evaluating at least one projection image, calibrating the robotic system based on the determined current position and orientation of the tip of the object, retrieving first information on a planned path section in the hollow organ on the basis of the current position of the object, determining the current relative position and relative orientation of the curved tip of the object relative to at least part of the hollow organ, retrieving second information on at least one relative position and relative orientation or relative position sequence and relative orientation sequence of the curved tip of the object or a similar object relative to at least part of the hollow organ used previously, for example during a navigation movement made before the method, along a path section in the hollow organ or another hollow organ, for example from a memory unit, and generating an actuation signal for actuating the robotic system. The actuation takes account of the first and second information and the current relative position and relative orientation of the tip relative to at least part of the hollow organ.

The method may prepare robot-assisted automatic or semi-automatic navigation of a medical object with a curved tip through a hollow organ of a patient in a simple manner, so that the subsequent navigation may be performed more precisely, more safely, in a more patient-friendly manner and with less risk of injury for the patient. Existing information regarding the relative position and relative orientation of the curved tip from navigations that have already been performed through path sections of the/a cavity organ is used to optimize a subsequent navigation based on this information. X-ray imaging the object in the cavity organ makes it possible to understand the current relative position and relative orientation of the curved tip relative to at least part of the hollow organ. According to an embodiment, the actuation includes single or multiple adaptation of the relative position and relative orientation of the curved tip relative to at least part of the hollow organ. In this context, the current relative position and relative orientation of the curved tip may be configured, changed and/or regulated as required, for example also with the aid of monitoring by X-ray imaging. This may, for example, be used in such a way that relative positions and relative orientations of the curved tip that have already proven themselves with a path section of the hollow organ (for example bending of the hollow organ in a certain direction, bifurcation of the hollow organ, outlet of the hollow organ at a certain position, etc.) are used again with the same or a similar path section, or, conversely, those which have resulted in delays or problems with navigation are avoided. Sequences of relative positions and relative orientations of the curved tip may be reused, modified, varied or avoided as required.

A patient's hollow organ should, for example, be understood to be a vessel (such as, for example, an artery or vein or a bronchus), a section of a vascular system or the entire vascular system of a patient.

The medical object may, for example, be a catheter or a guide wire with a curved tip. Information on the geometric shape of the tip of the object may for example also be obtained from a database or a memory and used if necessary. The shape of known catheter tips usually extends almost in one plane (i.e., almost two-dimensionally with only a very small extension into the third dimension) and also has a partially rounded or circular shape, for example a spiral ("pigtail"), with a single curvature or with a double curvature ("shepherd's hook"). Other shapes are also possible.

According to a further embodiment, an evaluation of the at least one projection image by at least one image processing algorithm or by a trained function is used to determine the current position and orientation of the curved tip of the object relative to at least part of the hollow organ. Thus, image processing algorithms such as, for example, object detection algorithms or edge detection algorithms may be used to detect the object in the projection image. For 3D position determination of the object and the orientation of the curvature of the tip, it is advantageous to acquire at least two projection images from two projection directions (distance preferably at least 30°), to detect the object therein and then to calculate a 3D reconstruction therefrom.

If only one projection image is available, a machine-learning algorithm may be used to determine the position and orientation of the curved tip of the object. The machine-learning algorithm may have been pre-trained using a plurality of projection images of catheter tips and the associated orientations. The machine-learning algorithm is, for example, based on neural networks, for example, a deep learning algorithm may be used. The position and orientation of the object and/or of the curved tip may then be used to determine the relative position and relative orientation of the object and/or its curved tip relative to the hollow organ or at least part of the hollow organ (for example, relative to the centerline, the vessel cross section, a branch, bend, etc.) in a known manner, as described above. It is also additionally possible to use a model of the shape of the curved tip in order to determine its orientation. The use of machine-learning algorithms may for example be advantageous when it is difficult to resolve the geometric relationships with normal image detection methods.

Initial calibration of the robotic system is, for example, performed based on the ascertained current position and orientation of the curved tip of the object. In this way, it is also possible to correct deviations from positions or orientations that were set or ascertained previously. Calibrations may also be performed several times at different times.

A relative position or orientation of the curved tip is considered relative to at least part of the hollow organ, i.e., for example, relative to the centerline or the cross section of the hollow organ or also relative to a branch or an outlet or bend of the hollow organ. Here, it is above all important that the hollow organ and the object have a common reference framework so that the position and orientation of the curved tip are comparable with different navigation movements. The determination of the relative position and relative orientation may also be included as part of the determination of the position and orientation if, for example, all coordinate systems (imaging system, robotic system and patient or hollow organ) are already registered at the beginning of the method. For example, a so-called pre-op, i.e., a volume image of the hollow organ recorded before the introduction of the object, may have been registered to the X-ray system before the recording of the projection images, so that the coordinate system of the imaging system and the hollow organ is already registered here. For example, this may be used as the basis for determining the relative position and relative orientation of the curved tip of the object relative to at least part of the hollow organ.

According to a further embodiment, the second information includes a relative position and relative orientation or relative position sequence and relative orientation sequence of the curved tip of the same or a similar object relative to at least part of the hollow organ used during a navigation retraction movement through at least one path section in the hollow organ or another, for example comparable, hollow organ. Thus, path sections previously traversed during retraction may also be used in this regard to actuate the relative position and relative orientation or relative position sequence and relative orientation sequence (in this case for example in reverse order). Relative positions and relative orientations of the curved tip that have proven themselves in a path section of the hollow organ (for example bending of the hollow organ in a certain direction, bifurcation of the hollow organ, outlet of the hollow organ at a certain position, etc.) during retraction may be used again in the same or a similar path section in forward movement, or conversely, it is also possible to avoid any that have led to delays or problems with navigation. Sequences of relative positions and relative orientations of the curved tip may be reused, modified, varied or avoided as required.

According to a further embodiment, the second information includes a suitability assessment of the relative position and relative orientation or relative position sequence and relative orientation sequence used during the navigation movement or navigation retraction movement. Here, suitability refers to the fact that the relative position/orientation is, for example, advantageous with regard to fast and/or obstacle-free and/or collision-free and/or patient-friendly navigation. The suitability assessment may be binary (suitable or unsuitable) or may be present in three or more gradations. In this context, it is for example favorable for safe and precise navigation for the second information to be taken into account in such a way that, in the event of a positive suitability assessment, the corresponding relative position and relative orientation or relative position sequence and relative orientation sequence is used and, in the event of a negative suitability assessment, the corresponding relative position and relative orientation or relative position sequence and relative orientation sequence is not used or modified. For this purpose, it is also possible for a gradated suitability assessment to be provided. According to a further embodiment, the second information is taken into account in such a way that, in the event of multiple positive suitability assessments, the corresponding relative position and relative orientation or relative position sequence and relative orientation sequence with the highest or best or most advantageous suitability assessment is used.

In order to be able to continuously further optimize the process, databases may be created with second information on different navigations (advancing and retraction movements). According to a further embodiment, the actuated relative position sequence and relative orientation sequence of the curved tip of the object relative to at least part of the hollow organ is stored in conjunction with the path section traversed in this way and a manual or automatic suitability assessment, for example in the memory unit. This enables such navigations to be performed in an increasingly safe and patient-friendly manner.

According to a further embodiment, a table, for example look-up table, is provided with a plurality of data items stored therein on navigation movements along path sections in hollow organs made before the method together with relative positions and relative orientations or relative position sequences and relative orientation sequences of curved tips of objects relative to at least part of the hollow organ used in the process from which the second information is taken. Herein, the table may also contain corresponding suitability assessments. The table may, for example, be stored locally or remotely in the memory unit or memory assembly. The data may also be processed by an algorithm, for example a machine-learning algorithm.

Embodiments provide a system for executing a method as cited above with a robotic system with at least one robot control unit and a robot-assisted drive system, the robot control unit being configured to generate an actuation signal for actuating robot-assisted navigation of a medical object, for example medical wire or catheter, with a curved tip in a hollow organ of a patient by the drive system, and an imaging system, for example an X-ray imaging system, for image monitoring of navigation with a radiation source and an image detector for recording projection images, for example X-ray projection images, a system control unit for actuating the imaging system and an evaluation unit for evaluating the projection images.

The overall system advantageously includes at least one memory unit for storing actuated relative position sequences and relative orientation sequences of the curved tip of the object relative to at least part of the hollow organ together with the path section traversed during a navigation movement or navigation retraction movement and optionally with a manual or automatic suitability assessment.

DETAILED DESCRIPTION

Figure 1:
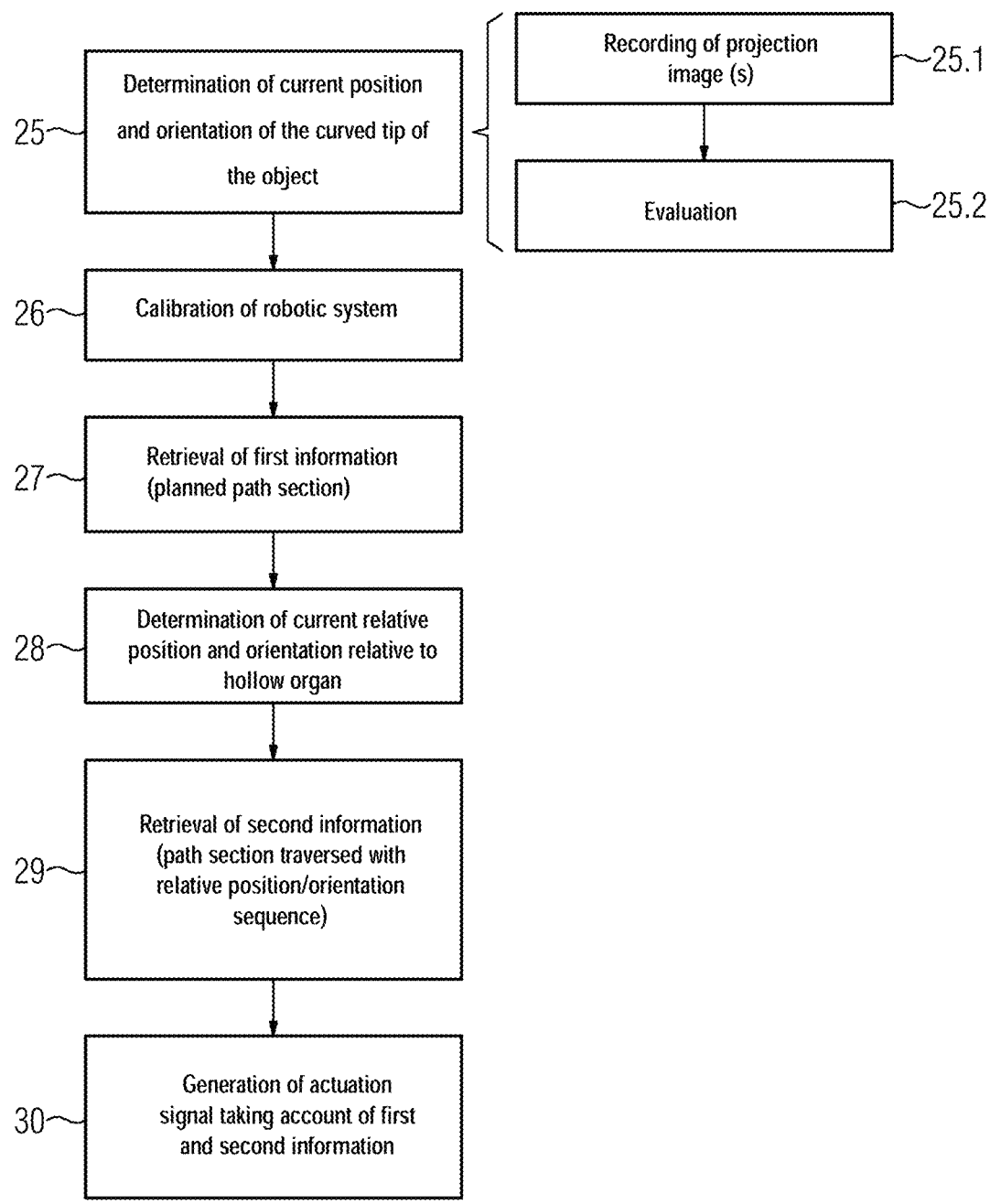
FIG. 1 depicts a sequence of steps of a method for generating an actuation signal for a robotic system according to an embodiment.
Figure 2:
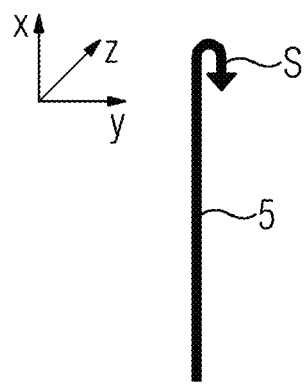
FIG. 2 depicts a view of a medical object with a curved tip according to an embodiment.
Figure 3:
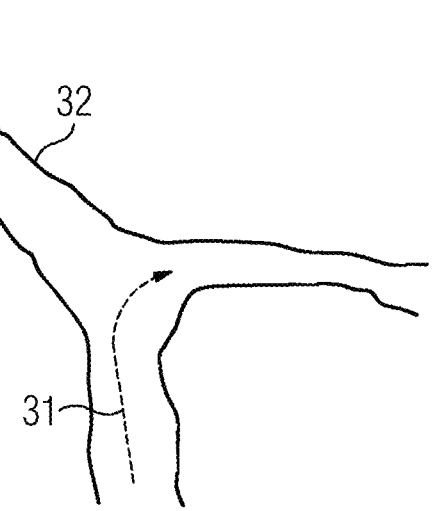
FIG. 3 depicts a view of a planned path section of a medical object in a hollow organ according to an embodiment.
Figure 4:
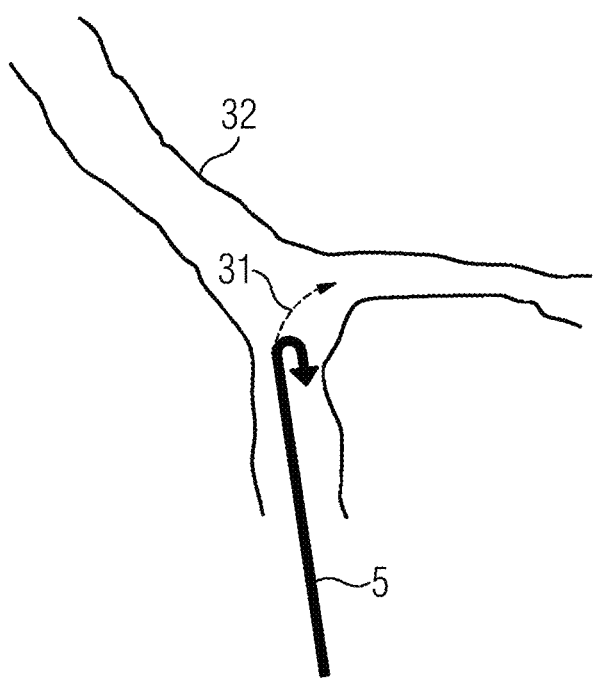
FIG. 4 depicts a view of a medical object with a curved tip in a hollow organ according to an embodiment.

FIG. 1 depicts a sequence of steps of a method for generating an actuation signal for a robotic system for robot-assisted navigation of a medical object 5 with a curved tip S in a hollow organ 32 of a patient. Herein, the method is performed with an overall system 1 including of a robotic system 2 and an X-ray system 10 for image monitoring—see FIG. 6. The medical object 5 may, for example, be a catheter or a guide wire with a curved tip S—see FIG. 2. It is a prerequisite of the method that the medical object 5 with the curved tip S in the hollow organ 32 is located in the body of a patient and it is planned that it is to be navigated there, for example, in order to perform an interventional procedure. For this purpose, for example, a path or path section 31 through the hollow organ 32 may be planned, as shown in FIGS. 3 and 4. During navigation, the curved tip S may, for example, perform a certain sequence of movements, for example a sequence of rotational movements R about its axis—see FIG. 5.

A hollow organ 32 of a patient may, for example, be understood to be a vessel (such as, for example, an artery or vein or a bronchus), a section of a vascular system or the entire vascular system of a patient. A relative position or orientation of the curved tip may be considered relative to at least part of the hollow organ, i.e., for example relative to the plane of the centerline of the hollow organ or to the cross section of the hollow organ or also relative to a branch or outlet or bend of the hollow organ.

The order of the steps is not binding and therefore a different order may also be provided where appropriate.

In a first step 25, a current position and current orientation of the curved tip S of the object 5 is determined, for example with regard to the image plane or the coordinate system of the imaging system. This may, for example, be performed by recording one or more projection images of the object 5 with the curved tip S introduced into the hollow organ by the X-ray system 10 in a first substep 25.1. The one or more projection images are then evaluated with respect to the position and orientation of the medical object 5 by an evaluation unit 20 in a second substep 25.2. Image processing algorithms such as, for example, object detection algorithms or edge detection algorithms of the evaluation unit 20 may be used to detect the object in the projection image. For a 3D position determination of the object with the orientation of the curved tip S, it is advantageous to acquire at least two projection images from two projection directions (distance preferably at least 30°), to detect the object in the projection images and then calculate a 3D reconstruction therefrom.

If, for example, only one projection image is available, a machine-learning algorithm may be used to determine the position and orientation of the curved tip of the object. The machine-learning algorithm may have been pre-trained with reference to a plurality of projection images of catheter tips and the associated orientations. The machine-learning algorithm is, for example, based on neural networks, for example, a deep learning algorithm may be used. It is then possible to determine the position and orientation of the object and/or its curved tip from the position and orientation of the object and/or the curved tip in a known manner, as described above. The use of machine-learning algorithms may also be advantageous when it is difficult to resolve the geometric relationships with normal image detection methods.

It is also additionally possible to use a model of the shape of the curved tip to determine the orientation of the curved tip.

Then, in a second step 26, initial calibration of the robotic system takes place, for example, based on the ascertained current position and orientation of the curved tip of the object, for example by a robot control unit 8. In this context, it is also possible to correct deviations from previously set positions or orientations. Calibrations may also be performed several times at different times.

In a third step 27, first information on a planned path section in the hollow organ is retrieved. The planned path section may, for example, be defined in path planning preceding the method, or it represents the path section to be covered subsequently starting from the current position of the object. The first information may, for example, be retrieved from a memory unit 35 assigned to the overall system or integrated therein or from a remote memory assembly (for example a cloud or information system) by a communication link. The planned path section may be of any length. For example, the path section may be complete path planning through a vascular system or it may be only a small part of such path planning, for example a movement along a bend in a vessel or a movement into a branch from one vessel into another vessel.

In a fourth step 28, the current relative position and relative orientation of the curved tip of the object relative to at least part of the hollow organ are determined, for example, relative to the plane or centerline of the hollow organ, the cross section of the vessel, a branch, bend, etc. Here, it is important that the hollow organ and the object have a common reference framework so that the position and orientation of the curved tip are comparable with different navigation movements. The determination of the relative position and relative orientation may also be included as part of the first step 25 (determination of position and orientation), if, for example, all coordinate systems (imaging system, robotic system and patient or hollow organ) are already registered at the beginning of the method. It is, for example, possible for a so-called pre-op, i.e., a volume image of the hollow organ recorded before the introduction of the object, to have been registered to the X-ray system, so the coordinate system of the imaging system and the hollow organ is already registered here. For example, this may be used as the basis for determining the relative position and relative orientation of the curved tip of the object relative to at least part of the hollow organ.

In a fifth step 29, second information is retrieved on at least one relative position and relative orientation or relative position sequence and relative orientation sequence of the curved tip of the object or a similar object relative to at least part of the hollow organ used previously, for example during a navigation movement made before the method, along a path section in the hollow organ or another hollow organ. Thus, the second information includes data on navigation movements that have already been made, for example forward movements or also backward movements, and the relative orientation in which an identical or similar object has already been moved through a similar or identical hollow organ. The second information may additionally include a suitability assessment of the relative position and relative orientation or relative position sequence and relative orientation sequence used during the navigation movement or navigation retraction movement made. Here, suitability refers to the suitability of the relative position/orientation with regard to fast and/or obstacle-free and/or collision-free and/or patient-friendly navigation, for example. The suitability assessment may be binary (suitable or unsuitable) or may be present in three or more gradations. The second information may, for example, be retrieved from a memory unit assigned to the overall system or integrated therein or from a remote memory assembly (for example a cloud or information system) by a communication link. For example, the relative position and orientation and a suitability assessment may be stored in the memory unit or memory assembly for each previously traversed path section, for example in a look-up table. It is also possible to use previously traversed path sections to obtain data that has been interpolated, extrapolated, simulated or optimized by a machine-learning algorithm, that is used as second information.

The third, fourth and fifth steps may, for example, be performed by the system control unit 16 and/or the robot control unit 8 or by both together with a communication link. There may also be an overall control unit for this purpose.

Then, in a sixth step 30, an actuation signal for actuating the robotic system is generated, wherein the actuation takes account of the first and second information and the current relative position and relative orientation of the tip relative to at least part of the hollow organ. The actuation signal is, for example, generated by the robot control unit 8. Thus, the information and data are used as the basis for optimizing a subsequent navigation. Thus, the actuation that may be affected by the actuation signal may include single or multiple adaptation or regulation of the relative position and relative orientation of the curved tip relative to at least part of the hollow organ. The current relative position and relative orientation of the curved tip may be configured, changed and/or regulated as required, for example also with the aid of monitoring by (X-ray) imaging. The information and data may, for example, be taken into account in such a way that relative positions and relative orientations of the curved tip that have already proven themselves with a path section of the hollow organ (for example bending of the hollow organ in a certain direction, bifurcation of the hollow organ, outlet of the hollow organ at a certain position, etc.) are used again with the same or a similar path section, or, conversely, those that have results in delays or problems with navigation are avoided. Sequences of relative positions and relative orientations of the curved tip may also be reused, modified, varied or avoided as required. For example, for a planned path section such as a branch from the iliac artery into the internal iliac artery, data on a similar navigation that has already been successful and the corresponding relative positions and orientations of a similar object used and its curved tip may be used to generate an actuation signal by which the curved tip of the object currently in use makes a similar movement, for example a certain rotational movement of the tip about its own axis.

In the event of a positive suitability assessment, it may be advantageous to use the corresponding relative position and relative orientation or relative position sequence and relative orientation sequence, while, in the event of a negative suitability assessment, it may be advantageous not to use, modify or vary the corresponding relative position and relative orientation or relative position sequence and relative orientation sequence. Thus, if, for the above example involving a branch from the iliac artery into the internal iliac artery, datasets are available on two navigation movements already made and different associated relative positions and orientations of a similar object used and its curved tip and there is a positive suitability assessment for a first dataset and a negative suitability assessment for the second dataset, the first dataset will be used. The actuation signal is then generated in such a way that the actuated movement uses the same relative positions and orientations of the curved tip of the current object as those known from the first dataset. This ensures that the execution of the navigation is successful, fast, collision-free and patient-friendly.

In the event of multiple positive suitability assessments with different suitability levels, the corresponding relative position and relative orientation or relative position sequence and relative orientation sequence with the highest ("most positive") suitability assessment may be used. This enables the navigation movement to be optimized. It is also possible to use and take account of data that has been interpolated, extrapolated, simulated or generated or changed by a machine-learning algorithm as second information.

For further optimization of the method, databases (for example tables, look-up table) may be created, supplemented or completed in the memory unit or memory assembly with second information on different navigations already made (advancing and retraction movements). The data collected in this way may then be accessed again in future methods. The actuated relative position sequence and relative orientation sequence of the curved tip of the object relative to at least part of the hollow organ together with the path section traversed in this way may for example also be stored with a manual or automatic suitability assessment. The manual suitability assessment may, for example, be input, supplemented or changed by a user. An automatic suitability assessment may, for example, take place in accordance with various criteria, for example speed or number of retraction movements, required. The additionally stored suitability assessment makes the navigation to be made increasingly safe and more patient friendly. The second information may also be processed and optimized by an algorithm, for example a machine-learning algorithm.

In addition, further calibrations may also be performed based on all the information.

Figure 5:
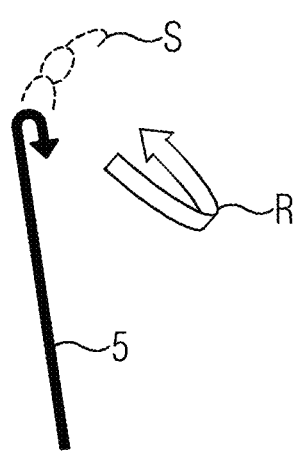
FIG. 5 depicts a view of an orientation-sequence of a curved tip of an object along a path section according to an embodiment.
Figure 6:
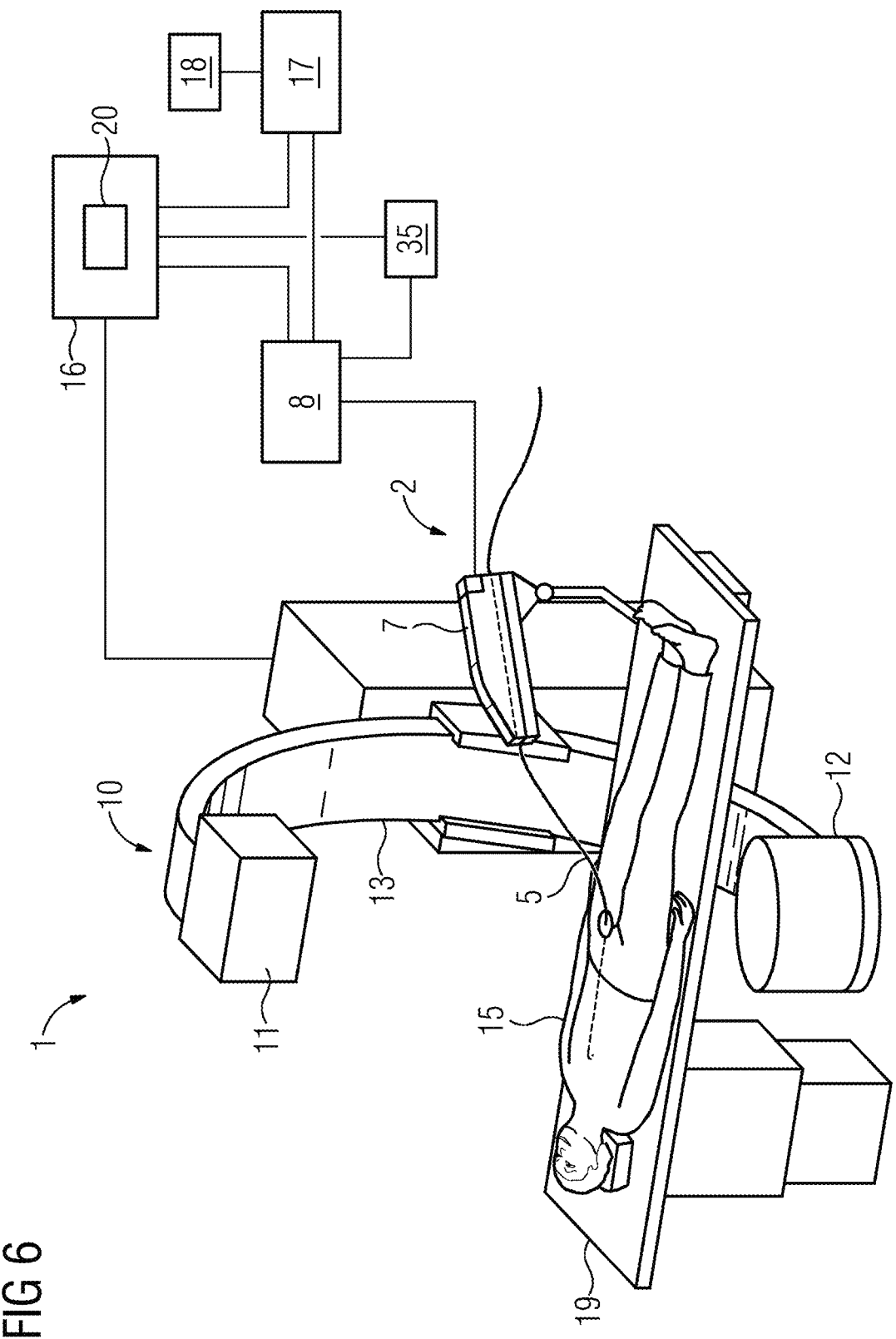
FIG. 6 depicts a view of an overall system for performing the method according to an embodiment.
Figure 7:
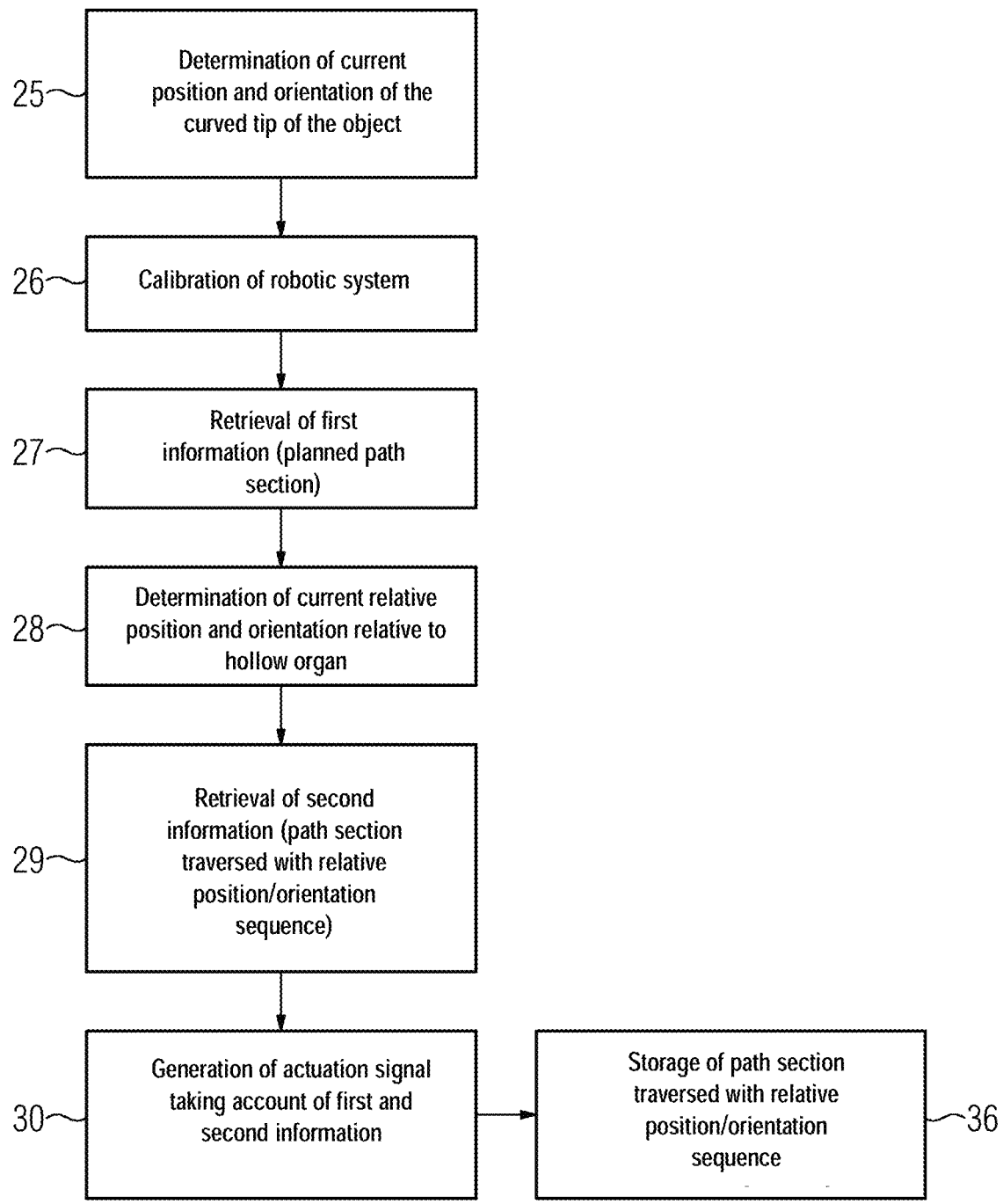
FIG. 7 depicts a further sequence of a method for generating an actuation signal for a robotic system according to an embodiment.

During navigation, the curved tip S may, for example, perform a certain sequence of movements, for example a sequence of rotational movements R, about its axis—see FIG. 5. The sequence may also be represented as a sequence of rotational angles.

The method enables robot-assisted automatic or semi-automatic navigation of a medical object with a curved tip through a hollow organ of a patient to be prepared in a simple manner, so that the subsequent navigation may be performed more precisely, more safely, in a more patient-friendly manner and with less risk of injury for the patient. In addition to possibly saving time, this may also reduce the likelihood of any complications.

The overall system 1 for performing the method has an imaging system in the form of an X-ray system 10 for recording X-ray projection images from different projection directions and a robotic system 2. The X-ray system 10 for recording X-ray projection images from different projection directions may, for example, be formed by a C-arm X-ray device, that is either mobile or permanently installed. The X-ray system 10 includes a C-arm 13 on which an X-ray source 12 and an X-ray detector 11 are arranged. A control unit 16, for example a computing unit with a processor, is provided for actuation. There is also an evaluation unit 20 for evaluating data and information. The robotic system 2 includes at least one robot control unit 8 and a robot-assisted drive system 7. The robot control unit 8 is configured to generate an actuation signal for actuating robot-assisted navigation of a medical object in a hollow organ of a patient. The overall system also includes a memory unit 35 for storing different types of image data and information. The system may also include a—not shown—communication apparatus for querying medical data or information from external memory assemblies or databases. In addition, a display unit 18 for displaying image data and an input unit 17 for receiving user input are assigned to the overall system 1. Additionally, or alternatively, there may be an overall system control unit.

Embodiments provide fast and safe navigation. A method is provided for generating an actuation signal for a robotic system for robot-assisted navigation of a medical object, for example medical wire or catheter, with a curved tip in a hollow organ of a patient. An X-ray system for image monitoring of the intervention is assigned to the robotic system, with the following steps: determining a current position and orientation of the curved tip of the object using the X-ray system, for example by recording and evaluating at least one projection image, calibrating the robotic system on the basis of the current position and orientation of the tip of the object determined, retrieving first information on a planned path section in the hollow organ on the basis of the current position of the object, determining the current relative position and relative orientation of the curved tip of the object relative to at least part of the hollow organ, retrieving second information on at least one relative position and relative orientation or relative position sequence and relative orientation sequence of the curved tip of the object or a similar object relative to at least part of the hollow organ used previously, for example during a navigation movement made before the method, along a path section in the hollow organ or another hollow organ, for example from a memory unit, and generating an actuation signal for actuating the robotic system, wherein the actuation takes account of the first and second information and the current relative position and relative orientation of the tip relative to at least part of the hollow organ.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating an actuation signal for a robotic system for robot-assisted navigation of an object with a tip in a hollow organ of a patient, wherein an imaging system for image monitoring of an intervention is assigned to the robotic system, the method comprising:
   determining a current position and a current orientation of the tip of the object using the imaging system;
   calibrating the robotic system based on the determined current position and current orientation of the tip of the object;
   retrieving first information on a planned path section in the hollow organ on a basis of the current position of the object;
   determining a current relative position and a current relative orientation of the tip of the object relative to at least part of the hollow organ;
   retrieving second information on at least one relative position and at least one relative orientation or relative position sequence and relative orientation sequence of the tip of the object or a similar object relative to at least part of the hollow organ used previously along a path section in the hollow organ or another hollow organ; and
   generating an actuation signal for actuating the robotic system, wherein the actuation takes account of the first and second information and the current relative position and the current relative orientation of the tip relative to at least part of the hollow organ.

2. The method of claim 1, wherein the actuation includes single or multiple adaptation of the relative position and the relative orientation of the tip relative to at least part of the hollow organ.

3. The method of claim 1, wherein actuated relative position sequence and relative orientation sequence of the tip of the object relative to at least part of the hollow organ is stored in conjunction with the path section traversed in this way.

4. The method of claim 3, wherein the actuated relative position sequence and relative orientation sequence of the tip of the object is stored in conjunction with the path section traversed in this way and a manual or automatic suitability assessment.

5. The method of claim 1, wherein an evaluation of at least one projection image by at least one image processing algorithm or by a trained function is used to determine the current position and the current orientation of the tip of the object.

6. The method of claim 1, wherein the second information includes a relative position and the relative orientation or the relative position sequence and the relative orientation sequence of the tip of the same or a similar object relative to at least part of the hollow organ used during a navigation retraction movement through at least one path in the hollow organ or another comparable hollow organ.

7. The method as of claim 6, wherein the second information includes a suitability assessment of the relative position and the relative orientation or the relative position sequence and the relative orientation sequence used during the robot-assisted navigation or navigation retraction movement.

8. The method of claim 7, wherein the second information is taken into account in such a way that in an event of a positive suitability assessment, the corresponding relative position and relative orientation or relative position sequence and relative orientation sequence is used or in an event of a negative suitability assessment, the corresponding relative position and relative orientation or relative position sequence and relative orientation sequence is not used.

9. The method of claim 8, wherein the second information is taken into account in such a way that, in an event of multiple positive suitability assessments, the corresponding relative position and the relative orientation or the relative position sequence and the relative orientation sequence with the best suitability assessment is used.

10. The method of claim 1, wherein a look-up table with a plurality of data items stored therein on navigation movements along path sections in hollow organs made before the method together with relative positions and relative orientations or relative position sequences and relative orientation sequences of curved tips of objects relative to at least part of the hollow organ used thereby is present from which the second information is taken.

11. The method of claim 10, wherein the data is processed by a machine-learning algorithm.

12. A system comprising:
a robotic system with at least one robot control unit and a robot-assisted drive system, the robot control unit configured to generate an actuation signal for actuating robot-assisted navigation of an object with a curved tip in a hollow organ of a patient by the robot-assisted drive system; and
an imaging system for image monitoring of navigation, the imaging system comprising a radiation source and an image detector for recording projection images, a system control unit for actuating the imaging system, and an evaluation unit for evaluating the projection images;
the imaging system configured to determine a current position and orientation of the curved tip of the object by recording and evaluating at least one projection image, calibrate the robotic system, retrieve first information on a planned path section in the hollow organ, determine a current relative position and a current relative orientation of the curved tip of the object relative to at least part of the hollow organ, retrieve second information on at least one relative position and at least one relative orientation or relative position sequence and relative orientation sequence of the curved tip of the object or a similar object relative to at least part of the hollow organ used previously along a path section in the hollow organ or another hollow organ, and generate an actuation signal for actuating the robotic system, wherein the actuation takes account of the first and second information and the current relative position and relative orientation of the curved tip.

13. The system of claim 12, further comprising:
at least one memory unit configured to store actuated relative position sequences and relative orientation sequences of the curved tip of the object relative to at least part of the hollow organ in conjunction with the path section traversed during a navigation movement or navigation retraction movement and optionally with a manual or automatic suitability assessment.

14. The system of claim 12, wherein the actuated relative position sequence and relative orientation sequence of the curved tip of the object relative to at least part of the hollow organ is stored in conjunction with the path section traversed in this way.

15. The system of claim 12, wherein an evaluation of at least one projection image by at least one image processing algorithm or by a trained function is used to determine the current position and the current orientation of the curved tip of the object.

16. The system of claim 12, wherein the second information includes a relative position and the relative orientation or the relative position sequence and the relative orientation sequence of the curved tip of the same or a similar object relative to at least part of the hollow organ used during a navigation retraction movement through at least one path in the hollow organ or another comparable hollow organ.

17. The system of claim 16, wherein the second information includes a suitability assessment of the relative position and the relative orientation or the relative position sequence and the relative orientation sequence used during the robot-assisted navigation or navigation retraction movement.

18. The system of claim 17, wherein the second information is taken into account in such a way that in an event of a positive suitability assessment, the corresponding relative position and relative orientation or relative position sequence and relative orientation sequence is used or in an event of a negative suitability assessment, the corresponding relative position and relative orientation or relative position sequence and relative orientation sequence is not used.

19. The system of claim 18, wherein the second information is taken into account in such a way that, in an event of multiple positive suitability assessments, the corresponding relative position and the relative orientation or the relative position sequence and the relative orientation sequence with the best suitability assessment is used.

* * * * *